(12) United States Patent
Terreno et al.

(10) Patent No.: US 9,007,458 B2
(45) Date of Patent: Apr. 14, 2015

(54) METHOD FOR MONITORING THE QUALITY OF THE PRIMER LAYER APPLIED TO A MOTOR-VEHICLE BODY PRIOR TO PAINTING

(75) Inventors: Andrea Terreno, Orbassano (IT); Giorgio Pasquettaz, Orbassano (IT)

(73) Assignee: C.R.F. Societa Consortile per Azioni, Orbassano (Torino) (IT)

( * ) Notice: Subject to any disclaimer, the term of this patent is extended or adjusted under 35 U.S.C. 154(b) by 483 days.

(21) Appl. No.: 13/596,491

(22) Filed: Aug. 28, 2012

(65) Prior Publication Data

US 2013/0147947 A1 Jun. 13, 2013

(30) Foreign Application Priority Data

Dec. 9, 2011 (EP) .................................... 11192716

(51) Int. Cl.
| | |
|---|---|
| H04N 7/18 | (2006.01) |
| G06T 7/00 | (2006.01) |
| G01N 21/95 | (2006.01) |
| B61L 23/04 | (2006.01) |
| A24C 5/34 | (2006.01) |

(52) U.S. Cl.
CPC .............. *G06T 7/0004* (2013.01); *B61L 23/044* (2013.01); *A24C 5/3412* (2013.01); *B61L 23/047* (2013.01); *G06T 7/0081* (2013.01); *G06T 2207/20021* (2013.01); *G06T 2207/20148* (2013.01); *G01N 21/9515* (2013.01); *G01N 2021/9518* (2013.01)

(58) Field of Classification Search
CPC ...... H04N 7/18; A24C 5/3412; B61L 23/044; B61L 23/047
USPC ........................................................ 348/128
See application file for complete search history.

(56) References Cited

U.S. PATENT DOCUMENTS

| | | | | |
|---|---|---|---|---|
| 4,863,268 A | * | 9/1989 | Clarke et al. | 356/237.2 |
| 4,920,385 A | * | 4/1990 | Clarke et al. | 356/237.2 |
| 5,237,404 A | * | 8/1993 | Tanaka et al. | 348/128 |
| 5,506,682 A | * | 4/1996 | Pryor | 356/623 |
| 5,566,244 A | | 10/1996 | Kato et al. | |
| 2004/0081347 A1 | | 4/2004 | Bernatek et al. | |
| 2010/0092069 A1 | | 4/2010 | Asada et al. | |

FOREIGN PATENT DOCUMENTS

KR 10-2009-0053079 5/2009

OTHER PUBLICATIONS

O. Ghita et al., "A Vision-Based System for Inspecting Painted Slates", Sensor Review, vol. 26, No. 2, pp. 108-115.
Search Report for EP 11192716 dated May 31, 2012.

\* cited by examiner

*Primary Examiner* — Michael Lee
(74) *Attorney, Agent, or Firm* — Nixon & Vanderhye, PC

(57) ABSTRACT

A method for monitoring the quality of the primer layer applied to the body of a motor vehicle prior to painting (enamelling) envisages provision of at least one manipulator robot carrying a monitoring head. The monitoring head includes a light source constituted by an array of LED sources and a videocamera that are held in a position fixed with respect to one another while they are displaced with respect to the surface to be monitored following the profile of said surface. The signals at output from the videocamera are processed by dividing the area monitored into an array of sub-areas and executing the same processing procedure simultaneously on all the sub-areas.

6 Claims, 5 Drawing Sheets

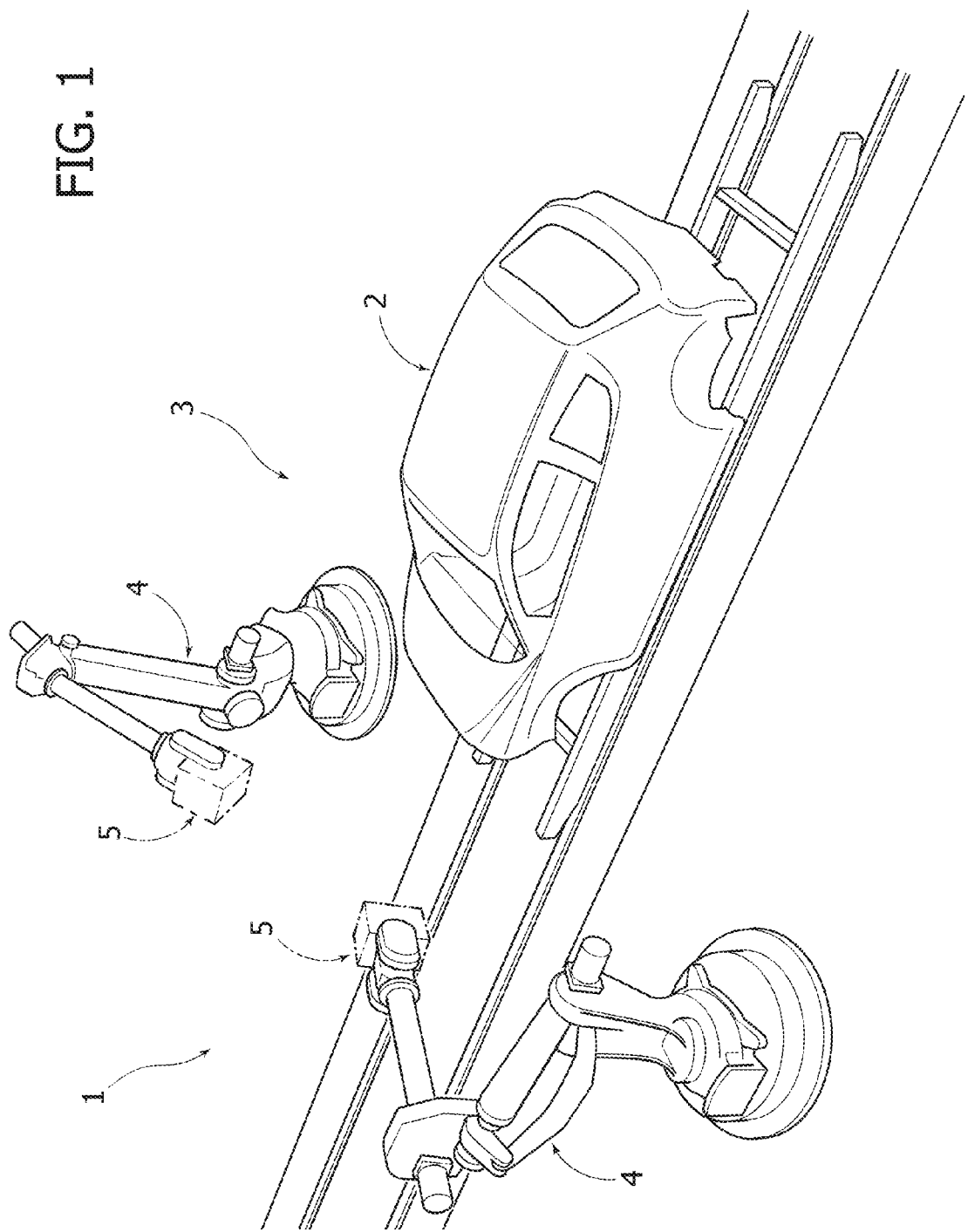

METHOD FOR MONITORING THE QUALITY OF THE PRIMER LAYER APPLIED TO A MOTOR-VEHICLE BODY PRIOR TO PAINTING

This application claims priority to EP 11192716.6 filed 9 Dec. 2011, the entire contents of each of which are hereby incorporated by reference.

FIELD OF THE INVENTION

The present invention relates to a method for monitoring the quality of the primer layer applied to a motor-vehicle body prior to painting (enamelling). In particular, the invention regards a method of the type comprising: provision of a light source for illuminating the surface to be monitored and of at least one videocamera for inspecting the illuminated surface; and processing of the signals at output from the videocamera to obtain information on the quality of the primer layer.

A method of the type specified above is, for example, known from the document No. KR 20090053079.

The primer layer applied on a motor-vehicle body can present different types of defects, which, after application of the enamel, can give rise to different effects. A first type of defects gives rise to a variation of the colour of the painted body, which can assume different appearances: non-uniform brightness, halos, stains or shadows, shiny parts, regions with shortage of paint. Other types of defects give rise to a non-uniform surface (orange-peel effect, stripes) or to accumulation of paint (running of paint).

The main class of defects of the primer layer is, however, constituted by defects of a localized type ("point defects") that take different forms (impurities, blistering, craters, degassing, flaking, peeling, pin-holing, streaking, scratches, porosities, blurring, bubbles). The method according to the invention is principally directed at monitoring defects of the latter type.

OBJECT OF THE INVENTION

The object of the invention is to provide a method that can be implemented with relatively simple and low-cost means, that will guarantee a high precision in the operation of monitoring, and that will enable the desired result to be obtained with a very low processing time.

SUMMARY OF THE INVENTION

With a view to achieving said object, the invention regards a method presenting the characteristics that have been referred to at the start and further characterized:

in that a manipulator robot is provided, which carries a monitoring head including both the aforesaid light source and the aforesaid videocamera, with said light source and said videocamera held in a fixed position with respect to one another;

in that said robot is controlled for moving the light source and the videocamera with respect to the surface monitored in a main direction of movement and according to a path parallel to the surface to be monitored, keeping the light source and the videocamera each at a constant distance from said surface in such a way that said path of movement follows a profile corresponding to the profile of said surface;

in that said light source is constituted by an array of LED sources designed to emit a beam of light on an area of the surface to be monitored so as to obtain a uniform intensity of illumination on the aforesaid surface;

in that said videocamera is positioned and oriented with respect to said light source in such a way as to collect by reflection the image of the illuminated area of the surface monitored;

in that the aforesaid processing step comprises:
dividing the area monitored into an array of sub-areas; and
executing the same processing procedure simultaneously on all the sub-areas, and in that the processing procedure executed for each sub-area comprises:

identifying regions of each sub-area with a luminosity lower than a threshold level as potential defects of the primer layer;

rejecting the potential defects that have dimensions smaller than a minimum threshold area or larger than a maximum threshold area, rejecting the potential defects that are distant from the edges of the sub-area by a length shorter than a threshold length; and identifying the potential defects that are not rejected following upon the aforesaid operations as confirmed defects, and classifying each confirmed defect as slight defect, medium defect, or serious defect, according to the area of the defect.

BRIEF DESCRIPTION OF THE DRAWINGS

The invention will now be described with reference to the annexed drawings, which are provided purely by way of non-limiting example and in which:

FIG. 1 is a schematic perspective view of a station for monitoring the quality of the primer layer applied on motor-vehicle bodies, on a production line;

DETAILED DESCRIPTION OF THE INVENTION

Figure 3:
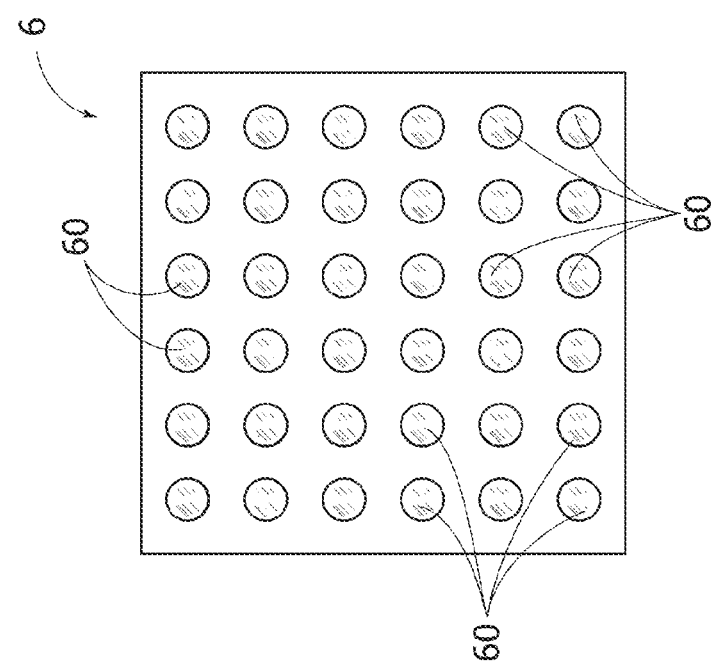
FIG. 3 is a schematic front view of the array of LED sources constituting the light source used in the method according to the invention.

In FIG. 1, the reference number 1 designates as a whole a production line, illustrated only schematically in the drawing, along which there advance motor-vehicle bodies 2 on which a primer layer has been applied, in preparation for the painting operation. The reference number 3 designates a station for monitoring the quality of the primer layer, comprising a pair of multi-axis manipulator robots 4, of any known type, pre-arranged at the two sides of the line 1 for analysing simultaneously the left-hand half and the right-hand half of the surface of each body 2. Each robot 4 has its distal wrist that carries a monitoring head 5 for execution of the method according to the invention.

Figure 2:
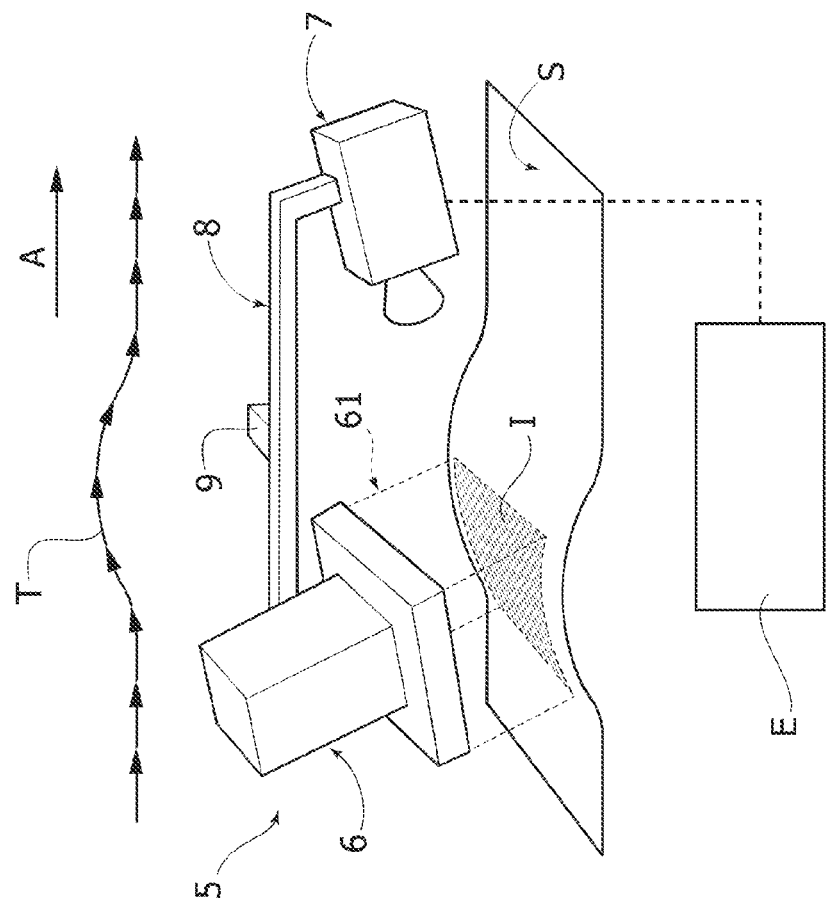
FIG. 2 is a schematic perspective view, which shows the essential components of the system used for implementation of the method according to the invention.

As illustrated schematically in FIG. 2, the monitoring head 5 comprises a light source 6 and a videocamera 7, which are supported in a pre-set fixed position with respect to one another by a supporting frame 8 having an attachment 9 of any known type (not illustrated) for fast connection to the wrist of the respective robot 4.

According to the invention, the electronic control unit of each robot 4 feeds the monitoring head 5 in the direction of advance A of the bodies 2 along the line 1, with a speed of advance higher than the speed of advance of the bodies 2, so as to create a relative movement between the monitoring head 5 and each body 2, sufficient for carrying out scanning of the entire surface of the body, preferably without the need to stop the body at the monitoring station 3. In the course of advance in the direction A, the monitoring head 5 is moved also in a direction orthogonal to the direction A so that it will follow a path T corresponding to the profile of the surface S to be monitored in such a way that both the light source 6 and the videocamera 7 remain constantly at the same distance from the surface S.

With reference to FIG. 3, the light source 6 comprises an orderly array of LED sources 60 that gives rise to a collimated beam of light 61 that illuminates an area I of the surface S with a light intensity substantially uniform in all the points of said area I.

The videocamera 7 is a CCD videocamera of any known conventional and standard type for detection of the image of the illuminated area I reflected by the surface S. For this purpose, the orientation of the source 6 and of the videocamera 7 is of course such as to guarantee the maximum optical efficiency, with the source 6 the optical axis of which is inclined by an angle preferably of between 20° and 30° with respect to the surface to be monitored S and the videocamera 7 is also inclined so as to be specular by a corresponding angle with respect to the surface itself.

The signals at output from the videocamera 7 are sent to an electronic processing unit E.

Figure 5:
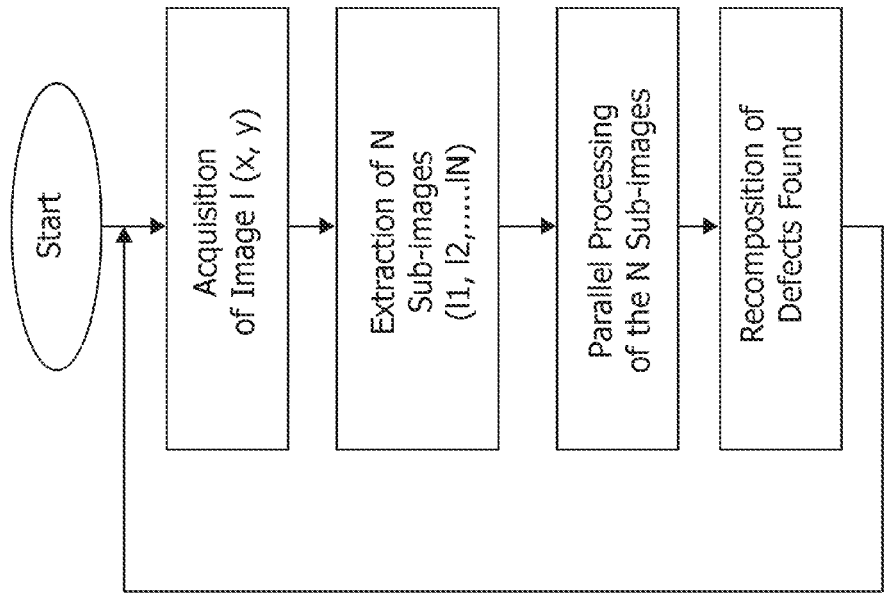
FIGS. 4 and 5 are block diagrams that illustrate the method according to the invention.
Figure 4:
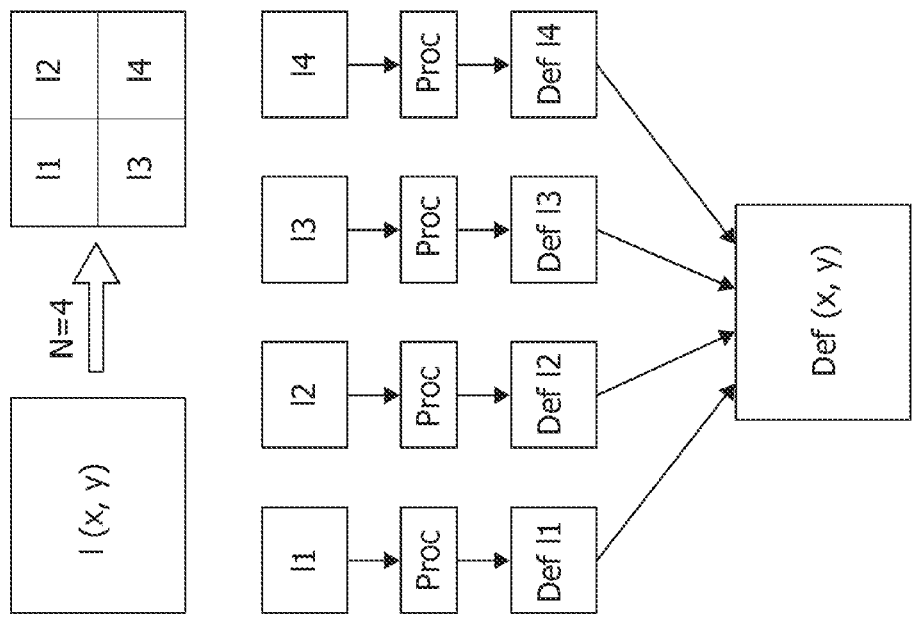

With reference to FIG. 7, in order to reduce as much as possible the processing time, the method according to the invention envisages that the area I (x, y) illuminated is divided into an array of sub-areas $I_1, I_2, \ldots I_N$. The example illustrated regards the case N=4, i.e., the division of the entire area I into four quadrants $I_1, I_2, I_3, I_4$. The images of the four sub-areas are processed simultaneously by the unit E in order to be able to identify simultaneously the defects of each of said sub-areas (see penultimate row of the block diagram of FIG. 4), after which the results obtained are united to obtain information on the defects of the entire area I. Said procedure is also clearly indicated in the block diagram of FIG. 5.

Figure 6:
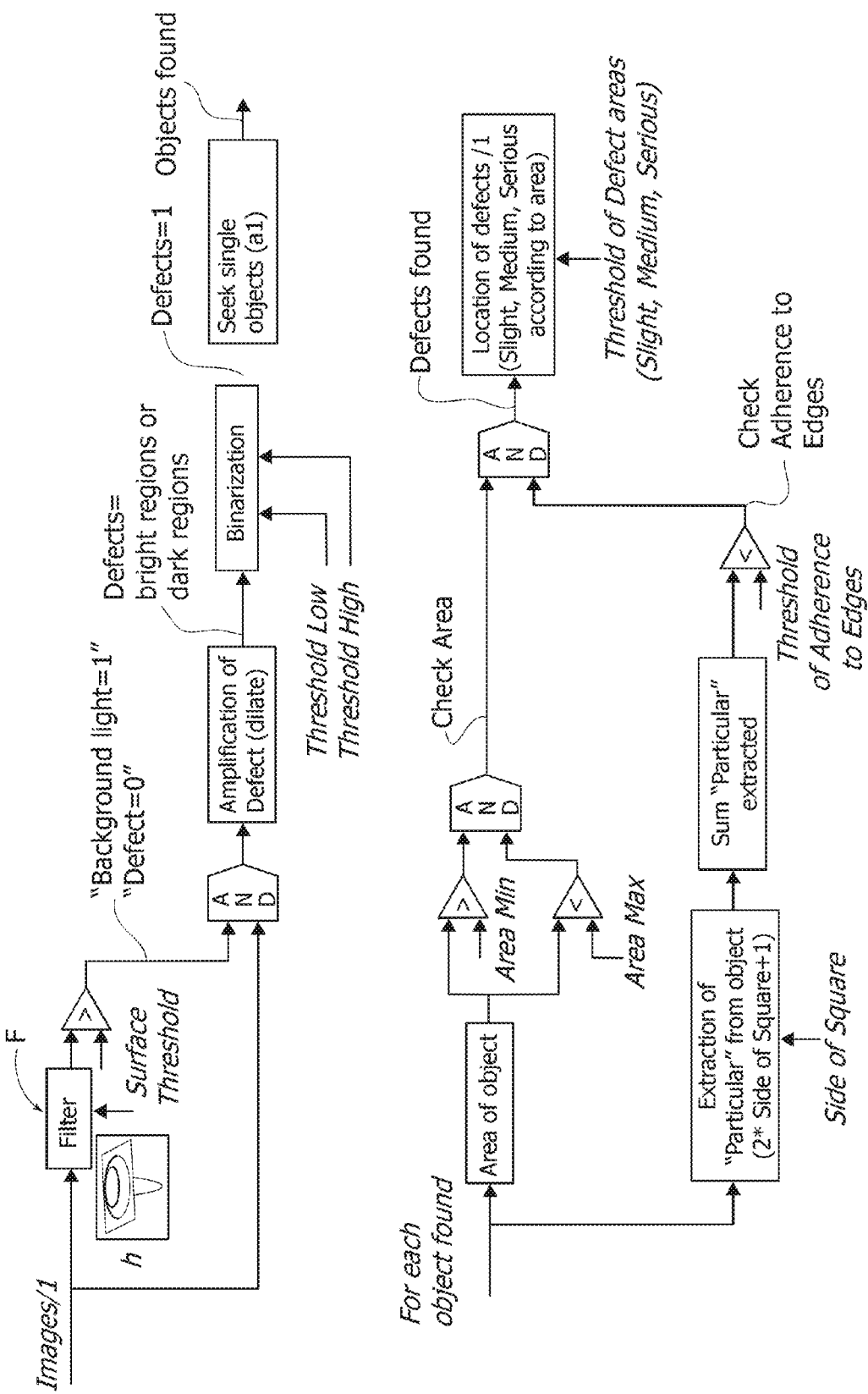
FIG. 6 illustrates further block diagrams that show the details of the method according to a preferred embodiment of the invention.

FIG. 6 shows block diagrams that illustrate a preferred embodiment of the processing method that is performed for each of the sub-images $I_1, I_2, \ldots I_N$ associated to the sub-areas into which the area I is divided.

The top part of FIG. 6 shows the step in which the regions of each sub-area with luminosity lower than a threshold level are identified as potential defects of the primer layer. For this purpose, a filter F, which is a kernel filter h $(m_1, m_2)$, is used $$y[n_1, n_2] = \sum_{m_1=0}^{N_1-1} \sum_{m_2=0}^{N_2-1} h[m_1, m_2] x[n_1 - m_1, n_2 - m_2]$$

where the kernel h $(m_1, m_2)$ used is a disk of radius 5:

| 0 | 0 | 0 | 0.0012 | 0.0050 | 0.0063 | 0.0050 | 0.0012 | 0 | 0 | 0 |
|---|---|---|---|---|---|---|---|---|---|---|
| 0 | 0.0000 | 0.0062 | 0.0124 | 0.0127 | 0.0127 | 0.0127 | 0.0124 | 0.0062 | 0.0000 | 0 |
| 0 | 0.0062 | 0.0127 | 0.0127 | 0.0127 | 0.0127 | 0.0127 | 0.0127 | 0.0127 | 0.0062 | 0 |
| 0.0012 | 0.0124 | 0.0127 | 0.0127 | 0.0127 | 0.0127 | 0.0127 | 0.0127 | 0.0127 | 0.0124 | 0.0012 |
| 0.0050 | 0.0127 | 0.0127 | 0.0127 | 0.0127 | 0.0127 | 0.0127 | 0.0127 | 0.0127 | 0.0127 | 0.0050 |
| 0.0063 | 0.0127 | 0.0127 | 0.0127 | 0.0127 | 0.0127 | 0.0127 | 0.0127 | 0.0127 | 0.0127 | 0.0063 |
| 0.0050 | 0.0127 | 0.0127 | 0.0127 | 0.0127 | 0.0127 | 0.0127 | 0.0127 | 0.0127 | 0.0127 | 0.0050 |
| 0.0012 | 0.0124 | 0.0127 | 0.0127 | 0.0127 | 0.0127 | 0.0127 | 0.0127 | 0.0127 | 0.0124 | 0.0012 |
| 0 | 0.0062 | 0.0127 | 0.0127 | 0.0127 | 0.0127 | 0.0127 | 0.0127 | 0.0127 | 0.0062 | 0 |
| 0 | 0.0000 | 0.0062 | 0.0124 | 0.0127 | 0.0127 | 0.0127 | 0.0124 | 0.0062 | 0.0000 | 0 |
| 0 | 0 | 0 | 0.0012 | 0.0050 | 0.0063 | 0.0050 | 0.0012 | 0 | 0 | 0 |

With reference once again to FIG. 6, the output of the filter (y(n1,n2)), presents the defects of the primer highlighted with low values (close to 0) and the background light with high values (close to 255). All the values of $y(n_1,n_2)$ lower than the threshold "Threshold Surface" are brought to the value 0 so that, after the AND operation ($z(n_1,n_2)$) represented in FIG. 6, we have either zero values (corresponding to probable defects) or the values of the original image $x(n_1,n_2)$.

Figure 7A:
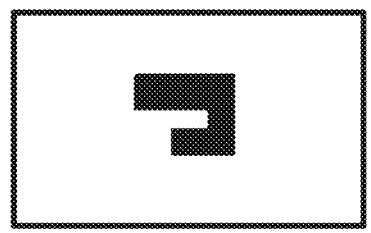
FIGS. 7A, 7B and 8A, 8B are schematic representations of defects analysed with the method according to the invention.
Figure 7B:
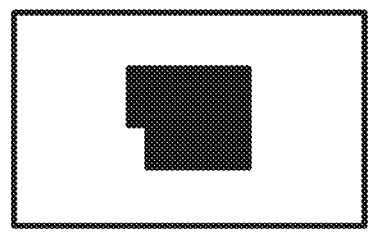

Once again with reference to the top part of FIG. 6, after the AND an "Amplification of Defects (Dilate)" is executed that enables amplification of the regions of the array $z(n_1,n_2)$ with zero values (probable defects) so that a probable defect is dilated. FIGS. 7A and 7B show a potential defect before and after the "Dilate" operation, respectively.

There is then executed an operation of "binarization" with two thresholds ("Threshold Low" and "Threshold High") that sends all the bright (illuminated) regions to the zero value and the probable defects to one.

The operation "seek objects" detects all the regions with value of unity (probable defects) and determines the area and the position of each object present in the binarized array.

With reference to the bottom part of FIG. 6, for each object found two checks are carried out to determine whether the object found (probable defect) is a real defect or not.

The first check verifies that the area of the object found is comprised between the thresholds "Area Min" and "Area Max" (objects that are too small or too big are rejected).

Figure 8A:
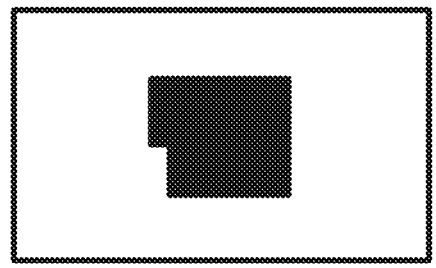
Figure 8B:
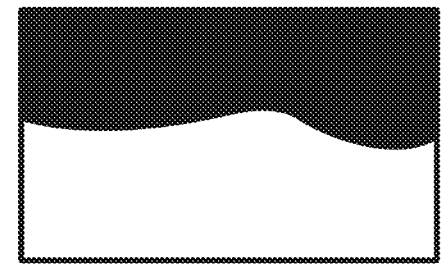

The second check extracts a square ("Particular") around the probable defect found for verifying that the particular extracted is isolated at the centre of the square, i.e., that it is at a distance from the edges of the sub-area monitored by a length greater than a threshold value. FIG. 8A shows the example of a defect that satisfies said condition, whilst FIG. 8B shows a potential defect that is to be rejected as real defect.

The potential defects that are not rejected following upon the aforesaid operations are considered confirmed defects.

For the confirmed defects the method according to the invention envisages a classification as slight, medium, or serious defects, according to their extension.

Of course, without prejudice to the principle of the invention, the details of construction and the embodiments may vary widely with respect to what has been described and illustrated herein purely by way of example, without thereby departing from the scope of the present invention, as defined in the annexed claims.

What is claimed is:

1. A method for monitoring the quality of the primer layer applied to the body of a motor vehicle prior to painting, said method comprising: provision of a light source for illuminating the surface to be monitored and at least one videocamera for inspecting the illuminated surface; and processing of the signals at output from the videocamera to obtain information on the quality of the primer layer, said method being characterized:

in that at least one manipulator robot is provided, carrying a monitoring head including both said light source and said videocamera, with said light source and said videocamera held in a position fixed with respect to one another, in that said robot is controlled for moving the light source and the videocamera with respect to the surface to be monitored in a main direction of movement and according to a path parallel to the surface to be monitored, keeping the light source and the videocamera each at a constant distance from said surface, in such a way that said path of movement follows a profile corresponding to the profile of said surface;

in that said light source is constituted by an array of LED sources designed to emit a beam of light onto an area of the surface to be monitored so as to obtain a uniform intensity of illumination on said surface;

in that said videocamera is positioned and oriented with respect to said light source in such a way as to collect by reflection the image of the illuminated area of the surface monitored;

in that the aforesaid processing step comprises:

dividing the monitored area into an array of sub-areas; and executing the same processing procedure simultaneously on all the sub-areas;

and in that the processing procedure executed for each sub-area comprises:

identifying regions of each sub-area with luminosity lower than a threshold level as potential defects of the primer layer;

rejecting the potential defects that have dimensions smaller than a minimum threshold area or larger than a maximum threshold area, rejecting the potential defects that are distant from the edges of the sub-area by a length shorter than a threshold length;

identifying the potential defects that are not rejected following upon the aforesaid operations as confirmed defects; and classifying each confirmed defect as slight defect, medium defect, or serious defect, according to the area of the defect.

2. The method according to claim 1, wherein the aforesaid step in which regions of each sub-area with luminosity lower than a threshold level are identified as potential defects of the primer layer is executed with the aid of a kernel filter designed to present the defects of the primer highlighted with low values close to zero and the background light with high values and in that all the values thus identified that are lower than a threshold value are brought to the zero value and represent the potential defects identified.

3. The method according to claim 2, wherein an operation of "Amplification of Defects (Dilate)" is executed, which amplifies the regions of an array z with zero values (probable defects) so that a probable defect is dilated.

4. The method according to claim 3, wherein following upon the operation of "Amplification of Defects (Dilate)" an operation of "Binarization" is executed with a lower threshold ("Threshold Low") and an upper threshold ("Threshold High"), designed to bring all the bright regions to the zero value, illuminated and to bring the potential defects to the value of unity.

5. The method according to claim 4, wherein after the operation of binarization an operation of "Seek Objects" is executed that detects all the regions with value of unity and determines the area and the position of each object present in the binarized array.

6. The method according to claim 1, wherein the aforesaid operation for rejection of the potential defects that are distant from the edges of the sub-area by a length shorter than a threshold length is executed by extracting a square ("Particular") around the potential defect found for verifying that the particular extracted is isolated at the centre of the square.

* * * * *